US011712484B2

(12) United States Patent
Braeckmans et al.

(10) Patent No.: US 11,712,484 B2
(45) Date of Patent: *Aug. 1, 2023

(54) CARBON-BASED PARTICLES FOR VAPOUR BUBBLE GENERATION

(71) Applicants: UNIVERSITEIT GENT, Ghent (BE); CENTRE NATIONAL DE LA RECHERCHE SCIENTIFIQUE CNRS, Paris (FR); UNIVERSITE DES SCIENCES ET TECHNOLOGIES DE LILLE 1, Villeneuve d'Ascq (FR)

(72) Inventors: Kevin Braeckmans, Daknam (BE); Stefaan De Smedt, Mariakerke (BE); Joseph Demeester, Ghent (BE); Sangram Keshari Samal, Ghent (BE); Ranhua Xiong, Ghent (BE); Sabine Szunerits, Villeneuve d'Ascq (FR); Rabah Boukherroub, Vlleneuve d'Ascq (FR)

(73) Assignees: UNIVERSITEIT GENT, Ghent (BE); CENTRE NATIONAL DE LA RECHERCHE SCIENTIFIQUE CNRS, Paris (FR); UNIVERSITE DES SCIENCES ET TECHNOLOGIES DE LILLE 1, Villeneuve d'Ascq (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/744,181

(22) PCT Filed: Jun. 29, 2016

(86) PCT No.: PCT/EP2016/065075
§ 371 (c)(1),
(2) Date: Jan. 12, 2018

(87) PCT Pub. No.: WO2017/009040
PCT Pub. Date: Jan. 19, 2017

(65) Prior Publication Data
US 2018/0200390 A1    Jul. 19, 2018

(30) Foreign Application Priority Data

Jul. 14, 2015 (EP) ..................... 15176560

(51) Int. Cl.
| | | |
|---|---|---|
| C01B 32/152 | (2017.01) | |
| C01B 32/182 | (2017.01) | |
| G10K 15/04 | (2006.01) | |
| A61K 49/22 | (2006.01) | |
| A61K 41/00 | (2020.01) | |
| C01B 32/15 | (2017.01) | |
| A61K 33/44 | (2006.01) | |
| A61K 47/02 | (2006.01) | |
| B82Y 5/00 | (2011.01) | |
| B82Y 15/00 | (2011.01) | |
| B82Y 40/00 | (2011.01) | |

(52) U.S. Cl.
CPC ............ *A61K 49/225* (2013.01); *A61K 33/44* (2013.01); *A61K 41/00* (2013.01); *A61K 41/0028* (2013.01); *A61K 47/02* (2013.01); *C01B 32/15* (2017.08); *G10K 15/046* (2013.01); *B82Y 5/00* (2013.01); *B82Y 15/00* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 2008/0070195 A1 | 3/2008 | Divito et al. | |
| 2014/0005537 A1* | 1/2014 | Asami | A61B 5/0095 600/431 |
| 2015/0150463 A1 | 6/2015 | Smeltzer et al. | |

FOREIGN PATENT DOCUMENTS

| | | |
|---|---|---|
| WO | 2006078987 A2 | 7/2006 |
| WO | 2009059215 A1 | 5/2009 |
| WO | 2014052449 A1 | 4/2014 |

OTHER PUBLICATIONS

Yan, Xin, Xiao Cui, and Liang-shi Li. "Synthesis of large, stable colloidal graphene quantum dots with tunable size." Journal of the American Chemical Society; 132.17 (2010): 5944-5945. (Year: 2010).*
Lim, Dong-Kwon, et al. "Enhanced photothermal effect of plasmonic nanoparticles coated with reduced graphene oxide." Nano letters 13.9 (2013): 4075-4079. (Year: 2013).*
Zhang, Liming, et al. "Functional graphene oxide as a nanocarrier for controlled loading and targeted delivery of mixed anticancer drugs." small 6.4 (2010): 537-544. (Year: 2010).*
"What is fluence?" from https://asi-pl.com.au/what-is-fluence/, accessed Jan. 27, 2020 (Year: 2020).*
Zhang T, Cui H, Fang CY, Su LJ, Ren S, Chang HC, Yang X, Forrest ML. Photoacoustic contrast imaging of biological tissues with nanodiamonds fabricated for high near-infrared absorbance. Journal of biomedical optics. Feb. 2013;18(2):026018. (Year: 2013).*
Chang IP, Hwang KC, Ho JA, Lin CC, Hwu RJ, Horng JC. Facile surface functionalization of nanodiamonds. Langmuir. Mar. 2, 2010; 26(5):3685-9. (Year: 2010).*

(Continued)

*Primary Examiner* — Nissa M Westerberg
(74) *Attorney, Agent, or Firm* — Workman Nydegger (57) ABSTRACT

A method for generating vapour bubbles in an object comprises introducing a composition into the object, the composition comprising carbon-based nano- or microparticles that can couple with a photon wave of electromagnetic radiation. The method also comprises irradiating said object using electromagnetic radiation. The irradiation thereby is adapted for using a set of carbon-based nano- or microparticles for subsequently forming first vapour bubbles and at least second vapour bubbles using the same carbon-based nano- or microparticles.

15 Claims, 3 Drawing Sheets

(56) References Cited

OTHER PUBLICATIONS

Kudryashov Sergey I et al. Photoacoustics of individual live cells and particles. InPhotons Plus Ultrasound: Imaging and Sensing 2006: The seventh Conference on Biomedical Thermoacoustics, Optoacoustics, and Acousto-optics Mar. 6, 2006 (vol. 6086, p. 60860J). International Society for Optics and Photonics (Year: 2006).*
Galanzha EI, Kim JW, Zharov VP. Nanotechnology-based molecular photoacoustic and photothermal flow cytometry platform for in-vivo detection and killing of circulating cancer stem cells. Journal of biophotonics. Dec. 2009;2(12):725-35. (Year: 2009).*
Khalili D. Graphene oxide: a promising carbocatalyst for the regioselective thiocyanation of aromatic amines, phenols, anisols and enolizable ketones by hydrogen peroxide/KSCN in water. New Journal of Chemistry. 2016;40(3):2547-53 and supplemental information (Year: 2016).*
Gallenkamp Type Melting point apparatus product page from https://crescendo.co.nz/, accessed Mar. 23, 2021 (Year: 2021).*
Galanzha EI, Kokoska MS, Shashkov EV, Kim JW, Tuchin VV, Zharov VP. In vivo fiber-based multicolor photoacoustic detection and photothermal purging of metastasis in sentinel lymph nodes targeted by nanoparticles. Journal of biophotonics. Sep. 2009;2(8-9 ):528-39. (Year: 2009).*
Wang S, Fu L, Xin J, Wang S, Yao C, Zhang Z, Wang J. Photoacoustic response induced by nanoparticle-mediated photothermal bubbles beyond the thermal expansion for potential theranostics. Journal of biomedical optics. Dec. 2018;23(12):125002. (Year: 2018).*
Kitz M, Preisser S, Wetterwald A, Jaeger M, Thalmann GN, Frenz M. Vapor bubble generation around gold nano-particles and its application to damaging of cells. Biomedical optics express. Feb. 1, 2011;2(2):291-304. (Year: 2011).*
Wu et al., "A Green Synthesis of Carbon Nanoparticles from Honey and Their Use in Real-Time Photoacoustic Imaging," Nano Research vol. 6 No. 5, 2013, pp. 312-325.
Moon et al., "Amplified Photoacoustic Performance and Enhanced Photothermal Stability of Reduced Graphene Oxide Coated Gold Nanorods for Sensitive Photoacoustic Imagining," American Chemical Society, vol. 9, No. 3, Mar. 9, 2015, pp. 2711-2719.
Wang et al., "Dye-Enhanced Graphene Oxide for Photothermal Therapy and Photoacoustic Imaging," Jounal of Materials Chemistry B, vol. 1, No. 42, Nov. 14, 2013, pp. 5762-5767.
Gong et al., "Carbon Nanotubes for Biomedical Imaging: The Recent Advances," Advanced Drug Delivery Reviews, vol. 65, No. 15, Oct. 30, 2013, pp. 1951-1963.
Smeltzer et al., "Alternative Approaches for the Diagnosis and Treatment of Staphylococcal Biofilm-Associated Infection." European Cells and Materials vol. 21, Suppl. 2, Jul. 2011, 1 Page.
Kang et al., "Cancer-Cell Targeting and Photoacoustic Therapy Using Carbon Nanotubes as "Bomb" Agents," Small, vol. 5, No. 11, Jun. 5, 2009, pp. 1292-1301.
European Search Report from EP Application No. EP 15176560.9, dated Jan. 14, 2016.
International Search Report and Written Opinion from PCT Application No. PCT/EP2016/065075, dated Sep. 16, 2016.
Prerona et al., "Delivery of Molecules into Cells Using Carbon Nanoparticles Activated by Femtosecond Laser Pulses", Nature Nanotechnology, vol. 5, No. 8, Jul. 18, 2010, pp. 607-611.
Sengupta et al., "Efficient Intracellular Delivery of Molecules with High Cell Viability Using Nanosecond-Pulsed Laser-Activated Carbon Nanoparticles", ACS Nano, vol. 5, Feb. 18, 2014, pp. 2889-2899.
Xiong et al.."Laser-Assisted Photoporation: Fundamentals, Technological Advances and Applications", Advances in Physics: X, vol. 1, No. 4, Sep. 12, 2016, pp. 596-620.
Office Action from corresponding EP Application No. EP 16733498.6, dated Mar. 24, 2020.

* cited by examiner

CARBON-BASED PARTICLES FOR VAPOUR BUBBLE GENERATION

FIELD OF THE INVENTION

The invention relates to the field of healthcare and biofouling. More specifically, the present invention relates to methods and systems using carbon-based particles for generating vapour bubbles, e.g. multiple vapour bubbles.

BACKGROUND OF THE INVENTION

Vapour bubbles can be induced by laser-irradiation of plasmonic nanoparticles that are located in hydrated tissue, as described in co-pending European patent application entitled "Disruption or alteration of microbiological film". The patent application describes that following absorption of the laser light, the nanoparticles become extremely hot so that the surrounding water evaporates, resulting in the formation of an expansive bubble. The mechanical force of expanding and collapsing vapour bubbles has been used to enable drug delivery into cells, to kill cells and to diagnose malaria. In addition, it is also described that vapor bubbles improve the delivery of antimicrobial agents deep into dense biofilms.

Until now, gold nanoparticles have been used the most for generating vapour bubbles. However, typically only one vapour bubble can be generated from a single gold nanoparticle, while some applications may benefit from the creation of more vapour bubbles from the same plasmonic particle.

There is still a need for methods and systems for efficient vapour bubble creation.

SUMMARY OF THE INVENTION

It is an object of the present invention to provide good and efficient methods and systems for generating vapour bubbles.

It is an advantage of embodiments of the present invention that a plurality of vapour bubbles can be generated using the same nano- or microparticle that is introduced in the object. The latter may have as an advantage that sustained action can be obtained.

It is an advantage of embodiments according to the present invention that the nano- or microparticles used can be easily be functionalized.

It is an advantage of some embodiments of the present invention that use graphene oxide based particles that they can be easily synthesized. It furthermore is an advantage that the fabrication can be performed in a cost efficient way.

It is an advantage of embodiments of the present invention that they provide good biocompatibility.

It is an advantage of embodiments of the present invention that by using carbon-based nano- or microparticles, that bubble formation can be performed in an efficient and improved way. It thereby is an advantage of the carbon-based nano- or microparticles that improved stability occurs during laser exposure so that multiple bubbles can be formed from the same particle by repeated laser irradiation.

It is an advantage of embodiments of the present invention that multiple bubble generation can be well used in drug delivery and therapeutic applications, as well as for diagnostic applications where one is interested in the acoustic signal coming from the vapour bubbles or light scattered by the vapour bubbles.

It is an advantage of some embodiments of the present invention making use of graphene oxide nanosheets that these have various chemical functional groups such as epoxy, hydroxyl and carboxy groups that offer the possibility of further functionalization to enhance the therapeutic potential. Graphene oxide has a high tendency to interact with aromatic compounds via strong noncovalent bonds including π-π-stacking, Van der Waals forces, hydrophobic interactions. Therapeutic agents can thus be physisorbed or via carbodiimide chemistry be positioned on the surface of graphene oxide and thus offer enhanced therapeutic potential. Graphene oxide sheets furthermore have a large surface that can be used for further chemical functionalization, such as coupling of drug molecules or functionalization of improved stability and targeting to particular tissues.

It is an advantage of embodiments of the present invention that the nano- or microparticles show the advantage of combining a very high melting temperature with the quality of efficiently absorbing radiation, e.g. laser light.

The present invention relates to a method for generating vapour bubbles in an object, the method comprising introducing a composition into the object, the composition comprising carbon-based nano- or microparticles that can couple with a photon wave of electromagnetic radiation and irradiating said object using electromagnetic radiation, wherein said irradiating is adapted for using a set of carbon-based nano- or microparticles for subsequently forming first vapour bubbles and at least second vapour bubbles using the same carbon-based nano- or microparticle, wherein the method is for altering or disrupting a microbiological film and/or for use in delivering compounds into biological cells and/or wherein the method further comprises killing of cells using said irradiation of said carbon-based nano- or microparticles. The method may be an in vitro or ex vivo method. The latter may refer also to treatment of tissue, isolated from the body. Introduction of the composition into the object can be performed by first obtaining the object and then introducing the carbon-based nano- or microparticles in the object or for example by introducing the composition during the formation of the object, e.g. during gelation of the object.

The carbon-based nano- or microparticles may be any of graphene particles, graphene oxide particles such as graphene oxide nanosheets, carbon nanotubes, carbon dots of fullerenes. It is an advantage of embodiments of the present invention that Graphene Oxide can be efficiently, easily and cost-effectively synthesised and are readily available. It is an advantage of embodiments of the present invention that carbon-based materials, such as for example graphene oxide, has proven to show good biocompatibility properties. It is an advantage of embodiments of the present invention that graphene based particles can be easily functionalised.

Said irradiating may comprise providing a plurality of irradiation pulses, wherein subsequent irradiation pulses on the carbon-based nano- or microparticles induce subsequent formation of vapour bubbles and/or wherein said irradiating comprises irradiating the carbon-based nano- or microparticles during an irradiation sequence and/or an irradiation time and/or at an irradiation intensity such that the heating of the carbon-based nano- or microparticles induces subsequent formation of vapour bubbles. It is an advantage of embodiments of the present invention that the irradiation source can be controlled such that the carbon-based nano- or microparticles can induce subsequent generation of vapour bubbles.

Said irradiating may comprise irradiating said object with a plurality of short pulses having a pulse duration of less than 10 ns. It is an advantage of embodiments of the present invention that heating of the carbon-based nano- or microparticles can be performed in an efficient way. Diffusion of heat is limited so that there is no or only limited damage to surroundings, untargeted parts of the object.

Said carbon-based nano- or microparticles may be functionalised. It is an advantage of embodiments of the present invention that graphene oxide and other carbon-based nanoparticles have a large surface that can be used for chemical functionalization, such as coupling of drug molecules or functionalisation for obtaining good, e.g. improved, stability, or functionalization for targeting.

Said carbon-based nanoparticles may be functionalised with drug molecules or targeting ligands, contrast agents, stabilising ligands. It is an advantage that a good colloidal stability can be obtained.

Said introducing may comprise allowing said carbon-based nanoparticles to diffuse into a microbiological film, and said forming may generate a mechanical force for locally altering or disrupting said microbiological film. It is an advantage of embodiments according to the present invention that an efficient method for disrupting microbiological films, such as for example bacterial films, is obtained. It furthermore is an advantage that a plurality of subsequent vapour bubble explosions can be induced, such that subsequent disrupting can be performed, avoiding that, if the disrupting force was insufficient to disrupt the whole film, the microbiological film recovers.

The method may be for use in delivering compounds into biological cells. The latter may for example be by creating pores in the cell membrane or cell wall, or by disrupting endosomes in case the compounds are taken up by endocytic processes. It is an advantage of methods according to embodiments of the present invention that controlled release of materials can be obtained by subsequently releasing materials upon subsequent irradiation pulses. In this way sustained release can be obtained. The delivery may be a single shot release or may be a release over time.

The method may be for use in killing cells, e.g. by causing lysing of cells.

The method furthermore may comprise detecting acoustic signals of the vapour bubbles or light scattered from the vapour bubbles for imaging the object. It is an advantage of embodiments of the present invention that a good imaging method can be obtained. It is an advantage that multiple vapour bubbles are created based on the same carbon-based nanoparticle, since the quality of the imaging is also based on the amount of acoustic signals that are generated.

In one aspect the present invention also relates to a method for generating vapour bubbles in an object, the method comprising introducing a composition into the object, the composition comprising carbon-based nano- or microparticles that can couple with a photon wave of electromagnetic radiation and irradiating said object using electromagnetic radiation, wherein said irradiating is adapted for using a set of carbon-based nano- or microparticles for subsequently forming first vapour bubbles and at least second vapour bubbles using the same carbon-based nano- or microparticle, wherein the method is for altering or disrupting a cell culture or biological tissue.

The present invention also relates to carbon-based nano- or microparticles for subsequently forming first and at least second vapour bubbles using the same carbon-based nano- or microparticles, for altering or disrupting a microbiological film and/or for use in delivering compounds into biological cells and/or for killing of cells.

The present invention furthermore relates to carbon-based nano- or microparticles for subsequently forming first and at least second vapour bubbles using the same carbon-based nano- or microparticles for altering or disrupting a microbiological film and/or for use in delivering compounds into biological cells and/or for killing of cells, for wound healing.

The present invention also relates to carbon-based nano- or microparticles for subsequently forming first and at least second vapour bubbles using the same carbon-based nano- or microparticles, for altering or disrupting a microbiological film and/or for use in delivering compounds into biological cells and/or for killing of cells, for cancer treatment.

The present invention furthermore relates to carbon-based nano- or microparticles for subsequently forming first and at least second vapour bubbles using the same carbon-based nano- or microparticles, for altering or disrupting a microbiological film and/or for use in delivering compounds into biological cells and/or for killing of cells, for treatment of skin infection.

The present invention also relates to carbon-based nano- or microparticles for imaging an object by imaging first and at least second vapour bubbles generated using the same carbon-based nano- or microparticles.

In the different aspects, the carbon-based nano- or microparticles may comprise any or a combination of graphene-oxide, graphene, carbon nanotubes, carbon dots and fullerenes.

The present invention also relates to a method for imaging an object or part thereof, the method comprising
directing an electromagnetic wave at the object comprising carbon-based nano- or microparticles, said electromagnetic wave being adapted for subsequently forming first vapour bubbles and at least second vapour bubbles using the same carbon-based nano- or microparticles.
detecting at least a first and a second set of vapour bubbles generated by carbon-based nano- or microparticles, and deriving an image from the detected at least a first and a second set of vapour bubbles.

In one aspect, the present invention relates to a method for generating vapour bubbles in an object, the method comprising introducing a composition into the object, the composition comprising carbon-based nano- or microparticles that can couple with a photon wave of electromagnetic radiation and irradiating said object using electromagnetic radiation thereby irradiating carbon-based nano- or microparticles for forming vapour bubbles. It is an advantage of embodiments of the present invention that vapour bubble formation can be performed in an efficient way.

The carbon-based nano- or microparticles may be any of graphene particles, graphene oxide particles such as graphene oxide nanosheets, carbon nanotubes, carbon dots of fullerenes. It is an advantage of embodiments of the present invention that Graphene Oxide can be efficiently, easily and cost-effectively synthesised and are readily available. It is an advantage of embodiments of the present invention that carbon-based materials, such as for example graphene oxide, has proven to show good biocompatibility properties. It is an advantage of embodiments of the present invention that graphene based particles can be easily functionalised.

Said carbon-based nano- or microparticles may be functionalised. It is an advantage of embodiments of the present invention that graphene oxide and other carbon-based nanoparticles have a large surface that can be used for chemical functionalization, such as coupling of drug molecules or functionalisation for obtaining good, e.g. improved, stability, or functionalization for targeting.

Said carbon-based nanoparticles may be functionalised with drug molecules or targeting ligands, contrast agents, stabilising ligands. It is an advantage that a good colloidal stability can be obtained.

Said introducing may comprise allowing said carbon-based nanoparticles to diffuse into a microbiological film, and said forming may generate a mechanical force for locally altering or disrupting said microbiological film. It is an advantage of embodiments according to the present invention that an efficient method for disrupting microbiological films, such as for example bacterial films, is obtained.

The method may be for use in delivering compounds into biological cells. The method may be used for the killing of cells, e.g. by lysing of cells.

The present invention also relates to a system for generating vapour bubbles in an object, the system comprising an irradiation source for irradiating carbon-based nano- or microparticles introduced in the object, and a controller programmed for controlling said irradiation such that vapour bubbles occur using the carbon-based nano- or microparticles.

The present invention also relates to carbon-based nano- or microparticles for forming vapour bubbles using the carbon-based nano- or microparticles, for altering or disrupting a microbiological film.

The present invention furthermore relates to carbon-based nano- or microparticles for forming vapour bubbles using the carbon-based nano- or microparticles, for wound healing.

The present invention also relates to carbon-based nano- or microparticles for forming vapour bubbles using the carbon-based nano- or microparticles, for cancer treatment.

The present invention furthermore relates to carbon-based nano- or microparticles for forming vapour bubbles using the carbon-based nano- or microparticles, for treatment of skin infection or apical periodontitis.

In the different aspects, the carbon-based nano- or microparticles may comprise any or a combination of graphene-oxide, graphene, carbon nanotubes, carbon dots and fullerenes.

The present invention relates to a method for generating vapour bubbles in an object, the method comprising introducing a composition into the object, the composition comprising graphene or graphene oxide nano- or microparticles that can couple with a photon wave of electromagnetic radiation and irradiating said object using electromagnetic radiation, wherein said irradiating is adapted for using a set of carbon-based nano- or microparticles for subsequently forming first vapour bubbles and at least second vapour bubbles using the same carbon-based nano- or microparticle. The method may be an in vitro or ex vivo method.

Introduction of the composition into the object can be performed by first obtaining the object and then introducing the graphene or graphene oxide nano- or microparticles in the object or for example by introducing the composition during the formation of the object, e.g. during gelation of the object.

It is an advantage of embodiments of the present invention that Graphene Oxide nano- or microparticles can be efficiently, easily and cost-effectively synthesised and are readily available. It is an advantage of embodiments of the present invention that carbon-based materials, such as for example graphene oxide, has proven to show good biocompatibility properties. It is an advantage of embodiments of the present invention that graphene based particles can be easily functionalised.

Said irradiating may comprise providing a plurality of irradiation pulses, wherein subsequent irradiation pulses on the graphene or graphene oxide nano- or microparticles induce subsequent formation of vapour bubbles and/or wherein said irradiating comprises irradiating the carbon-based nano- or microparticles during an irradiation sequence and/or an irradiation time and/or at an irradiation intensity such that the heating of the graphene or graphene oxide nano- or microparticles induces subsequent formation of vapour bubbles. It is an advantage of embodiments of the present invention that the irradiation source can be controlled such that the graphene or graphene oxide nano- or microparticles can induce subsequent generation of vapour bubbles.

Said irradiating may comprise irradiating said object with a plurality of short pulses having a pulse duration of less than 10 ns. It is an advantage of embodiments of the present invention that heating of the graphene or graphene oxide nano- or microparticles can be performed in an efficient way. Diffusion of heat is limited so that there is no or only limited damage to surrounding, untargeted parts of the object.

Said graphene or graphene oxide nano- or microparticles may be functionalised. It is an advantage of embodiments of the present invention that graphene or graphene oxide nanoparticles have a large surface that can be used for chemical functionalization, such as coupling of drug molecules or functionalisation for obtaining good, e.g. improved, stability, or functionalization for targeting.

Said graphene or graphene oxide nanoparticles may be functionalised with drug molecules or targeting ligands, contrast agents, stabilising ligands. It is an advantage that a good colloidal stability can be obtained.

Said introducing may comprise allowing said graphene or graphene oxide nanoparticles to diffuse into a microbiological film, and said forming may generate a mechanical force for locally altering or disrupting said microbiological film. It is an advantage of embodiments according to the present invention that an efficient method for disrupting microbiological films, such as for example bacterial films, is obtained. It furthermore is an advantage that a plurality of subsequent vapour bubble explosions can be induced, such that subsequent disrupting can be performed, avoiding that, if the disrupting force was insufficient to disrupt the whole film, the microbiological film recovers.

The method may be for use in delivering compounds into biological cells. The latter may for example be by creating pores in the cell membrane or cell wall, or by disrupting endosomes in case the compounds are taken up by endocytic processes. It is an advantage of methods according to embodiments of the present invention that controlled release of materials can be obtained by subsequently releasing materials upon subsequent irradiation pulses. In this way sustained release can be obtained. The delivery may be a single shot release or may be a release over time.

The method may be for use in killing cells, e.g. by causing lysing of cells.

The method furthermore may comprise detecting acoustic signals of the vapour bubbles or light scattered from the vapour bubbles for imaging the object. It is an advantage of embodiments of the present invention that a good imaging method can be obtained. It is an advantage that multiple vapour bubbles are created based on the same carbon-based nanoparticle, since the quality of the imaging is also based on the amount of acoustic signals that are generated.

The present invention also relates to a system for generating vapour bubbles in an object, the system comprising an irradiation source for irradiating graphene or graphene oxide nano- or microparticles introduced in the object, and a controller programmed for controlling said irradiation such that it is adapted for generating irradiation such that subsequent formation of first vapour bubbles and at least second vapour bubbles occurs using the same graphene or graphene oxide nano- or microparticles.

The controller may be programmed for generating subsequent irradiation pulses on the graphene or graphene oxide nano- or microparticles for inducing subsequent formation of vapour bubbles and/or for generating irradiating of the graphene or graphene oxide nano- or microparticles during an irradiation sequence and/or an irradiation time and/or at an irradiation intensity such that the heating of the graphene or graphene oxide nano- or microparticles induces subsequent formation of vapour bubbles. It is an advantage of embodiments of the present invention that the irradiation source can be controlled such that the graphene or graphene oxide nano- or microparticles can induce subsequent generation of vapour nano- or microbubbles.

The system furthermore may comprise an optics or acoustics based detection system for detecting at least a first and a second set of vapour bubbles generated by graphene or graphene oxide nano- or microparticles and a controller for deriving an image based on the detection system.

The present invention also relates to graphene or graphene oxide nano- or microparticles for subsequently forming first and at least second vapour bubbles using the same graphene or graphene oxide nano- or microparticles, for altering or disrupting a microbiological film.

The present invention furthermore relates to graphene or graphene oxide nano- or microparticles for subsequently forming first and at least second vapour bubbles using the same graphene or graphene oxide nano- or microparticles, for wound healing.

The present invention also relates to graphene or graphene oxide nano- or microparticles for subsequently forming first and at least second vapour bubbles using the same graphene or graphene oxide nano- or microparticles, for cancer treatment.

The present invention furthermore relates to graphene or graphene oxide nano- or microparticles for subsequently forming first and at least second vapour bubbles using the same carbon-based nano- or microparticles, for treatment of skin infection.

The present invention also relates to graphene or graphene oxide nano- or microparticles for imaging an object by imaging first and at least second vapour bubbles generated using the same carbon-based nano- or microparticles.

The present invention also relates to a method for imaging an object or part thereof, the method comprising
directing an electromagnetic wave at the object comprising graphene or graphene oxide nano- or microparticles, said electromagnetic wave being adapted for subsequently forming first vapour bubbles and at least second vapour bubbles using the same graphene or graphene oxide nano- or microparticles,
detecting at least a first and a second set of vapour bubbles generated by carbon-based nano- or microparticles, and
deriving an image from the detected at least a first and a second set of vapour bubbles.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes. Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Where in embodiments of the present invention reference is made to subsequent generation of vapour bubbles by the same nano- or microparticles, reference is made to the situation where there is at least one nano- or microparticle that individually subsequently generates different vapour bubbles. In other words, the nano- or microparticle does not disappear after generation of the first vapour bubble, but can upon irradiation generate a second vapour bubble or third vapour bubble.

Where in embodiments of the present invention reference is made to altering and/or disrupting of microbiological films, reference is made to both situations where one alters the density of the biological film, e.g. decreases the density of the microbiological film or "loosen" the film without disrupting it or where one at least partially or completely disrupts the film.

Where reference is made to vapour bubbles, reference is made to vapour bubbles having a diameter in the range 10 nm to 100 µm.

Where reference is made to diffusible particles, reference is made to particles that are able to diffuse into the microbiological film through Brownian motion. At least 10%, e.g at least 30%, e.g. at least 50% of the particles may be able to diffuse into the microbiological film, e.g. diffuse into the microbiological film over at least 1 µm. The diameter of such particles may be small with respect to the pores in the film.

In a first aspect, the present invention relates to a method for generating vapour bubbles in an object. The object may be a living human being, a synthetic biomaterial, a non-living object, a microbiological film, etc. The method may be used for a variety of applications such as for example for loosening or destroying microbiological films, for imaging of an object, for optoporation, for drug delivery, for treatment of wound infections, for treatment of apical periodontitis, for cancer therapy, for skin treatment, . . . . The method according to embodiments of the present invention comprises introducing a composition into the object. Such introducing can be performed in a plurality of ways. It may include allowing the composition to diffuse into the microbiological film following topical administration (dispensing, flowing over) or actively depositing the composition into the microbiological film, such as by injecting the composition into the object. The nano- or microparticles therefore are in some embodiments diffusible particles. Introducing the composition in the object also may include introducing the particles during generation of the object, i.e. for example during gelation of the object.

According to embodiments of the present invention, the particles are carbon-based nano- or microparticles. The nano- or microparticles fulfil the requirement of having an electron density that can couple with a photon wave of electromagnetic radiation. Different surface charges may be applied, such as for example the structure may be anionic, neutral or cationic. The nano- or microparticles may have a diameter between 1 nm and 1 µm, e.g. 20 to 200 nm. Such particles are adapted such that they can couple with a photon wave of electromagnetic radiation. The carbon-based nano- or microparticles may for example be graphene oxide based particles such as for example graphene oxide sheets or carbon particles such as for example carbon nanotubes or carbon dots, or may for example be fullerenes.

In some embodiments, the particles may have a functionalized surface. Such surface functionalization may be any suitable surface functionalization such as for example for improving colloidal stability, for obtaining a certain surface charge, for coupling of antimicrobial agents, for targeting, . . . .

The method also comprises, according to embodiments of the present invention, Irradiating the object using electromagnetic radiation. The irradiation thereby is adapted for using a set of carbon-based nano- or microparticles for subsequently forming first vapour bubbles and at least second vapour bubbles using the same carbon-based nano- or microparticles. Such vapour bubbles typically may be water vapour bubbles caused by heating of water around the carbon-based nano- or microparticles. The irradiation may advantageously be a pulsed irradiation, although embodiments of the present invention are not limited thereto and in principle also a continuous wave irradiation could be used. In the advantageous embodiments wherein pulsed irradiation is used, the pulses may have a duration in the range 10 ns downto 0.1 ns or downto 0.1 ps. The fluence may be adapted depending on the pulse duration. In one example, the fluence may be at least 10 or tens mJ per pulse. The wavelength of the radiation used may range from UV to the IR region. In some applications, the wavelength range of the radiation used may be in the near infrared. According to embodiments, the irradiation is such that subsequently different vapour bubbles are created due to the heating of the same carbon-based nano- or microparticles. Embodiments of the present invention not being limited thereto, an illustration of how parameters of the irradiation can be determined or optimised will be discussed further in the description.

The irradiation thereby is performed such that the heating of the nanoparticles results in the subsequent generation of mechanical forces when the subsequently formed vapour bubbles expand and/or collapse. It is to be noticed that the vapour bubbles do not need to explode or implode but that also stable cavitation may cause an altering or disrupting effect. According to aspects of the present invention, altering or disrupting may not only be performed in biofilms, but also in cell cultures or biological tissue.

When the thermal energy of the carbon-based nano- or microparticles is consumed, the vapour bubble may violently collapse, causing local mechanical forces by high-pressure shock waves. Due to the thermal isolation of the vapour bubbles (typically <10 μs), the diffusion of heat into the environment is negligible so that almost all energy of the irradiated carbon-based nano- or microparticles is converted to mechanical energy (expansion of the vapour bubbles) without heating of the environment. This property makes vapour bubbles an interesting phenomenon to cause local mechanical damage, create an acoustical signal, or more generally cause a local action without causing unspecific thermal damage to the environment, thus making it useful for use in or nearby healthy tissue.

Embodiments of the present invention furthermore have the advantage of possibly generating multiple vapour bubbles using the same nano- or microparticle. The latter provides advantages such as requiring less particles to create a same number of vapour bubbles, providing the possibility of sustained generation of mechanical forces and thus for example sustainable delivery of compounds, sustainable delivery of mechanical forces and therefore for example sustainable action on keeping a microbiological film in a less dense shape.

In one embodiment, the present invention also is used for performing optoporation, i.e. providing access to the interior of a cell using optical energy.

In another embodiment, the present invention also relates to the use of multiple vapor bubble generation for imaging purposes. The expansion and/or collapse of the vapour bubbles can be detected using an optical or acoustical detector. In this way, the vapour bubbles can be monitored. As the vapour bubbles are generated in different concentrations depending on the concentration of the water content or as vapour bubbles are generated around the carbon-based nanoparticles and the carbon-nanoparticles may be functionalized as to bind to particular tissue or cells, images of such regions, tissues or cells can be obtained.

In one set of embodiments, the method according to embodiments of the present invention furthermore may comprise providing nanomedicine formulations of antimicrobial agents using vapour bubbles. Such a release can, when applied in the context of a microbiological film, be done by applying both the step of inducing disruption or loosening of a microbiological film using vapour bubbles and providing nanomedicines to the infected region. The latter results in the advantageous effect that the nanomedicines can get more easily to the infected region, since the microbiological film is disrupted and cannot act as a diffusion barrier. It thus is found that by physically altering and/or disrupting the microbiological clusters, nanomedicines can more easily reach deep cell layers, resulting in an improved treatment efficacy. Alternatively nanomedicines also may be delivered at particular positions, in or outside a microbiological film, by disrupting a container wherein the nanomedicines are placed. The antimicrobial agents may be encapsulated in containers, the containers being for example liposomes, lipids or polymer based nanoparticles. The carbon-based nano- or microparticle may be linked thereto, i.e. they may be encapsulated in the containers or may be bound to a surface thereof. The container may have an outer diameter less than or equal to 1 μm. Alternatively, the antimicrobial agents also may be bound directly to the nano- or microparticles.

An advantage of being able to subsequently create mechanical forces is that a controlled and sustained release of nanomedicines can be obtained by subsequently releasing nanomedicines by subsequently disrupting containers containing the nanomedicines, without the need for administering new nano- or microparticles. An example of such nanomedicines are liposomes encapsulating AMA. One example is Arikayce, a liposomal formulation of amikacin for inhalation by CF patients that is currently in clinical phase III trials. Another example is Repithel, a liposomal formulation of PVP-I that is used for the treatment of wound infections.

The above are examples of delivery of compounds to biological cells.

According to some embodiments, the method may also be used for the killing of cells, e.g. by lysing of cells, using said irradiation of said carbon-based nano- or microparticles.

According to one aspect, the present invention also relates to a system for generating vapour bubbles in an object. The system comprises an irradiation source for irradiating carbon-based nano- or microparticles introduced in the object, and a controller programmed for controlling said irradiation such that it is adapted for generating irradiation such that subsequent formation of first vapour bubbles and at least second vapour bubbles occurs using the same carbon-based nano- or microparticles. The irradiation sequence and/or an irradiation time and/or irradiation intensity may thereby be selected such that the heating of the carbon-based nano- or microparticles induces subsequent formation of vapour bubbles. According to some embodiments, the system furthermore comprises an optics or acoustics based detection system for detecting at least a first and a second set of vapour bubbles generated by carbon-based nano- or microparticles. Based on the detection a processor or controller may derive an image from the measured signals.

In one aspect, the present invention also relates to carbon-based nano- or microparticles for subsequently forming first and at least second vapour bubbles using the same carbon-based nano- or microparticles, for altering or disrupting a microbiological film. The present invention also relates to carbon-based nano- or microparticles for subsequently forming first and at least second vapour bubbles using the same carbon-based nano- or microparticles, for wound healing. In yet another aspect, the present invention relates to a carbon-based nano- or microparticles for subsequently forming first and at least second vapour bubbles using the same carbon-based nano- or microparticles, for cancer treatment, e.g. melanoma. The present invention also relates to carbon-based nano- or microparticles for subsequently forming first and at least second vapour bubbles using the same carbon-based nano- or microparticles, for treatment of skin infection. The present invention furthermore relates to carbon-based nano- or microparticles for subsequently forming first and at least second vapour bubbles using the same carbon-based nano- or microparticles, for treatment of apical periodontitis. The carbon-based nano- or microparticles comprise any or a combination of graphene-oxide, graphene, carbon nanotubes, carbon dots and fullerenes. The carbon-based nano- or microparticles may be as described in the first aspect.

In still another aspect, the present invention relates to a particular method of imaging an object or part thereof, the method comprising directing an electromagnetic wave at the object comprising carbon-based nano- or microparticles, said electromagnetic wave being adapted for subsequently forming first vapour bubbles and at least second vapour bubbles using the same carbon-based nano- or microparticles, detecting at least a first and a second set of vapour bubbles generated by carbon-based nano- or microparticles, and deriving an image from the detected at least a first and a second set of vapour bubbles.

Figure 1:
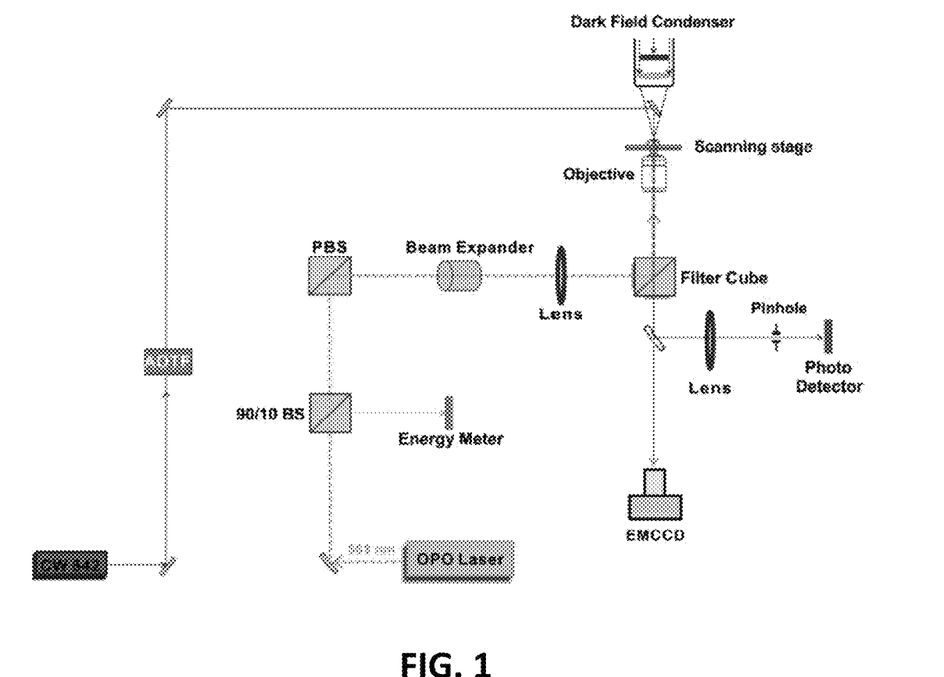
FIG. 1 shows an optical setup for generation and detection of vapour bubbles generated using graphene oxide nanoparticles, for illustrating advantages of embodiments of the present invention

By way of illustration, embodiments of the present invention not being limited thereto, an example is shown of generation of multiple vapour bubbles using a same graphene oxide particle. The measurements were performed using an optical system including an electric timer, for optically heating of the graphene oxide particles and for detecting of the vapour bubbles. By way of illustration, an exemplary system for performing the measurements is described in FIG. 1. FIG. 1 shows a pulsed laser with a pulse duration of ~7 ns tuned at a wavelength of 561 nm (Opolette HE 355 LD, OPOTEK Inc., CA, USA) which was used to generate and detect the vapor nanobubbles induced by the heating of the graphene oxide. The pulsed laser is equipped with an Optic Parametric Oscillator that allows tuning of the wavelength. A dark-field microscope was used to capture scattered light of the vapour nanonbubbles, the dark field microscope being furthermore equipped with a CW laser and photodiode for vapour bubble lifetime measurements. An acousto-optic modulator is used for controlling the power of the continuous wave laser. The lifetime of the vapour nanobubbles typically is short, depending on their size. In view thereof, the camera (EMCCD camera, Cascade II: 512, Photometrics, Tucson, Ariz., USA) was synchronized with the pulsed laser by an electronic pulse generator (BNC575, Berkeley Nucleonics Corporation, CA, USA). The pulse laser sends a Q-switch signal to trigger the pulse generator and also trigger the camera at a certain delay. BS refers to a laser beam splitter reflecting 10% of the radiation and transmitting 90% of the radiation. PBS is a polarization beam splitter.

Figure 2:
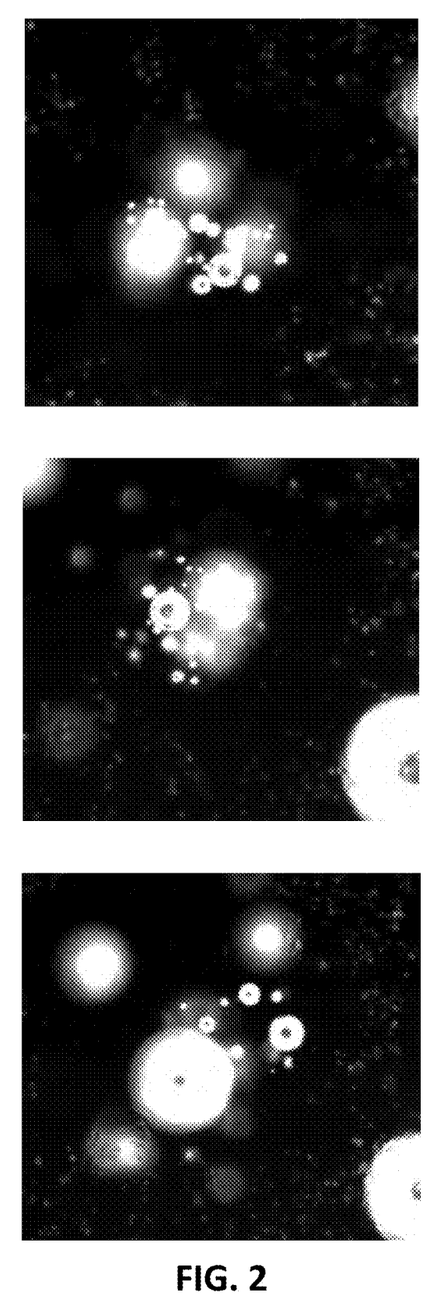
FIG. 2 illustrates images at different moments in time during or after irradiation of the graphene oxide particles, illustrating the principle of multiple bubble generation according to embodiments of the present invention.

In FIG. 2 images are shown of the generation of vapour bubbles after/during irradiation of the vapour bubbles. Graphene oxide particles were introduced in water. The graphene oxide nanosheets were about 200 nm sized. The fluence used was 0.5 J/cm$^2$ and the pulse duration was around 9 nanoseconds with a pulse duration interval of 0.2 seconds. Three different images are shown at different moments in time of the irradiation of the graphene oxide nanosheets and it was seen that subsequent generation of vapour bubbles caused by the same particles could be established. In the images, the removal of vapour bubbles by collapsing over time can be seen, as well as the generation of new vapour bubbles over time.

By way of illustration, embodiments of the present invention not being limited thereto, an example is discussed wherein formation of multiple successive vapour nanobubbles (VNB) from graphene quantum dots is shown. The experiment was compared with the situation wherein gold nanoparticles were used.

Figure 3:
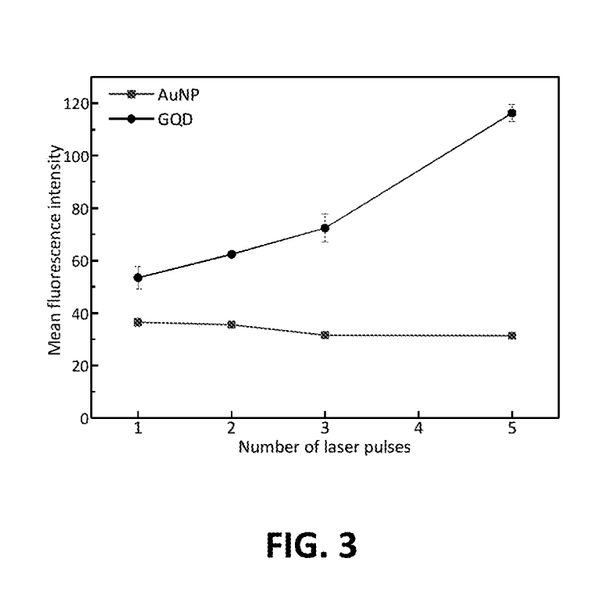
FIG. 3 illustrates gradually increased delivery of a fluorescent compound into cells by the subsequent bubble generation as function of multiple laser pulses, according to embodiments of the present invention.

HeLa cells were seeded in a 96 well plate at 15.000 cells per well. After 24 h a suspension of cationic 70 nm AuNP in PBS buffer was added to the cells at a concentration of 0.2 µg/mL. After 30 min incubation, the cells were washed to remove unbound AuNP and new cell medium was added. 0.2 mg/ml FITC-dextran 40 kDa (FD40) was added to the cell medium as a fluorescent reporter for the photoporation delivery experiment. When cells are photoporated FD40 will diffuse through the membrane pores into the cells and will render them fluorescent. Photoporation was performed with 7 ns laser pulses at 561 nm with a laser fluence of 0.5 J/cm$^2$. The laser illumination was provided in such a way that each cell in the well receives a discrete predefined number of laser pulses, ranging from one pulse to 5 pulses per cell. Finally, cells were trypsinized and their fluorescence was measured by flow cytometry. As can be seen from FIG. 3, cells become loaded with FD40 after the first pulse. Since multiple VNB formation is not possible with AuNP, no further FD40 loading into the cells is observed when multiple pulses are applied.

Instead, when using Graphene Quantum Dots (GQD) as an example of a carbon based nanomaterial, multiple VNB can be formed from the same GQD. Consequently, cells can become gradually more loaded with FD40 when multiple laser pulses are applied, as can be seen from FIG. 3. The experimental conditions were exactly the same as for the gold nanoparticles, except that GQD were applied to cells at a concentration of 10 µg/ml and the laser fluence was reduced to 0.27 J/cm$^2$ since the VNB threshold is less for these nanoparticles.

The above example illustrates that vapour nanobubbles can induce pores in the membrane of cells when they are formed around AuNP that are in close proximity to the cell membrane. This is useful to deliver cell-impermeable substances, such as nucleic acids, through the membrane pores into the cytoplasm of cells. Since VNB can only be formed one time from AuNP, this means that repeated photoporation of cells with the same batch of AuNP is not possible. When using graphene quantum dots, it can be seen that successive vapour nanobubbles can be generated from the same nanoparticles.

By way of illustration, an example of how to determine irradiation parameters for generating a vapour nanobubble is demonstrated below.

Figure 4:
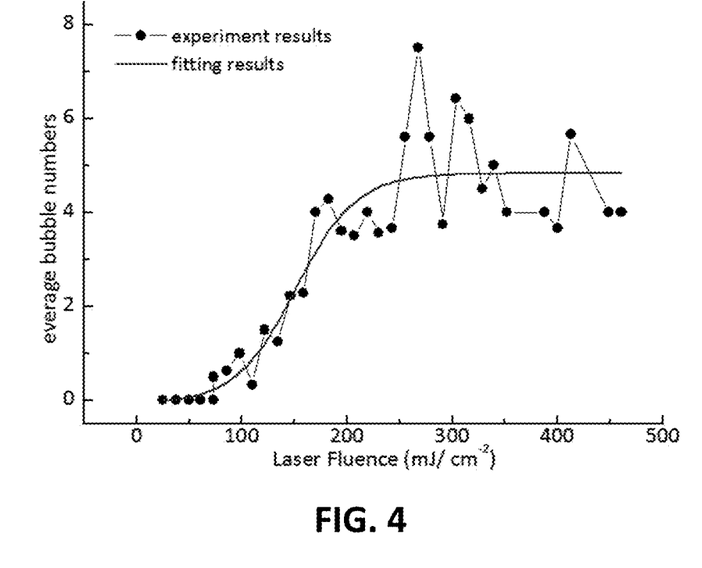
FIG. 4 illustrates experimental determination of the threshold for the laser fluence for generating vapour nanobubbles from graphene quantum dots, as can be used in embodiments according to the present invention.

For nanoparticles of interest, the threshold intensity for forming vapour nanobubbles is evaluated. The nanoparticles of interest in the present example were obtained as follows: A 1 mg/mL graphene quantum dots (GQDs) solution was diluted 100 times in distilled water. 1 mL of the solution was incubated in a microscopy recipient for 1 h allowing GQDs to partially adhere to the glass substrate. Laser pulses at 561 nm were subsequently applied at increasing laser fluence levels from 20 to 470 mJ/cm$^2$ covering a circular area of approximately 200 µm diameter. Dark field images were recorded before applying a laser pulse and immediately after when vapour nanobubbles are formed. Vapour nanobubbles can be clearly seen in dark field microscopy due to their enhanced light scattering. FIG. 4 shows the average number of vapour nanobubbles that are observed after applying a single laser pulse as a function of the laser fluence. The vapour nanobubble threshold is defined as the laser fluence at which there is 90% certainty that a bubble will be formed from a nanoparticle. For the GQD used here it is approximately 225 mJ/cm$^2$.

It will be clear for the person skilled in the art that similar experiments for other nanoparticles, for other laser wavelengths, for other laser pulse durations and/or for other dispersion media can easily be performed, thus allowing the skilled person to determine the laser fluence to be used for specific particles.

The invention claimed is:
1. A method for use in delivering compounds into biological cells and/or for killing of cells using irradiation of carbon-based nano- or microparticles and/or for locally altering or disrupting a microbiological film by generating vapour bubbles in an object, the method comprising:
  introducing a composition into the object, the composition comprising carbon-based nano- or microparticles that can couple with a photon wave of electromagnetic radiation, the carbon-based nano- or microparticles comprising any or a combination of graphene-oxide, graphene, carbon nanotubes or carbon dots, irradiating said object using electromagnetic radiation, wherein said irradiating comprises irradiation with a plurality of pulses and is adapted for using a set of carbon-based nano- or microparticles for forming first vapour bubbles and subsequently forming at least second vapour bubbles, wherein one of the first vapour bubbles and one of the at least second vapour bubbles is formed using the same carbon-based nano- or microparticle within the set of carbon-based nano- or microparticles, said irradiating comprising irradiating the carbon-based nano- or microparticles during an irradiation sequence and an irradiation time and at an irradiation intensity such that the heating of the carbon-based nano- or microparticles induces subsequent formation of vapour bubbles, wherein each of the plurality of pulses has a laser fluence greater than or equal to a threshold intensity, said threshold intensity defined as the laser fluence at which there is a 90% certainty that a bubble will be formed from said carbon-based nano- or microparticles.

2. A method for generating vapour bubbles according to claim 1, wherein said method is an in vitro or ex vivo method.

3. A method for generating vapour bubbles according to claim 1, wherein said carbon-based nano- or microparticles are graphene oxide particles.

4. A method for generating vapour bubbles according to claim 1, wherein said irradiating comprises providing the plurality of irradiation pulses, wherein subsequent irradiation pulses on the carbon-based nano- or microparticles induce subsequent formation of vapour bubbles and/or wherein said irradiating comprises irradiating the carbon-based nano- or microparticles during an irradiation sequence and/or an irradiation time and/or at an irradiation intensity such that the heating of the carbon-based nano- or microparticles induces subsequent formation of vapour bubbles.

5. A method for generating vapour bubbles according to claim 1, wherein said carbon-based nanoparticles are functionalised with drug molecules or targeting ligands, contrast agents, and/or stabilising ligands.

6. A method for generating vapour bubbles according to claim 1, wherein
said introducing comprises allowing said carbon-based nanoparticles to diffuse into a microbiological film, and
said forming generating a mechanical force for locally altering or disrupting said microbiological film.

7. A method for generating vapour bubbles according to claim 1, wherein the method furthermore comprises detecting acoustic signals of the vapour bubbles for imaging the object.

8. A method for generating vapour bubbles according to claim 1, wherein each of the plurality of pulses has a duration of less than 10 ns.

9. A method for generating vapour bubbles according to claim 1, wherein each of the nano- or microparticles have a diameter between 1 nm and 1 µm.

10. A method for generating vapour bubbles according to claim 1, wherein the threshold intensity is determined by applying a plurality of pulses with a fluence that increases from one pulse to the next.

11. A method for generating vapour bubbles according to claim 1, wherein the vapour bubbles have a diameter in the range of 10 nm to 100 µm.

12. A method for generating vapour bubbles according to claim 9, wherein each of the nano- or microparticles have a diameter between 20 nm and 200 nm.

13. A method for generating vapour bubbles according to claim 1, wherein a wavelength of the plurality of pulses is within an IR region.

14. A method for generating vapour bubbles in an object, the method comprising:
determining a threshold intensity for forming vapour bubbles from carbon-based nano- or microparticles that can couple with a photon wave of electromagnetic radiation, by applying laser pulses at increasing fluence levels from 20 to 470 mJ/cm$^2$ to said carbon-based nano- or microparticles until reaching the threshold intensity at which there is a 90% certainty that a bubble will be formed,
introducing a composition into the object, the composition comprising said carbon-based nano- or microparticles, the carbon-based nano- or microparticles comprising graphene-oxide, graphene, carbon nanotubes or carbon dots,
irradiating said object using electromagnetic radiation, wherein said irradiating comprises irradiation with a plurality of pulses and is adapted for using a set of carbon-based nano- or microparticles for forming first vapour bubbles and subsequently forming at least second vapour bubbles, wherein one of the first vapour bubbles and one of the at least second vapour bubbles is formed using the same carbon-based nano- or microparticle within the set of carbon-based nano- or microparticles,
wherein said object comprises a biological system, and the method is for use in delivering compounds into biological cells and/or for killing of cells using said irradiation of said carbon-based nano- or microparticles and/or for locally altering or disrupting a microbiological film, and
wherein each of the plurality of pulses has a laser fluence greater than or equal to the threshold intensity.

15. A method for generating vapour bubbles in an object, the method comprising:
introducing a composition into the object, the composition comprising carbon-based nano- or microparticles that can couple with a photon wave of electromagnetic radiation, the carbon-based nano- or microparticles comprising graphene-oxide,
irradiating said object using electromagnetic radiation, wherein said irradiating comprises irradiation with a plurality of pulses and is adapted for using a set of carbon-based nano- or microparticles for forming first vapour bubbles and subsequently forming at least second vapour bubbles, wherein one of the first vapour bubbles and one of the at least second vapour bubbles is formed using the same carbon-based nano- or microparticle within the set of carbon-based nano- or microparticles,
wherein said object comprises a biological system, and the method is for use in delivering compounds into biological cells and/or for killing of cells using said irradiation of said carbon-based nano- or microparticles and/or for locally altering or disrupting a microbiological film, and
wherein each of the plurality of pulses has a fluence of 500 mJ/cm$^2$, a pulse duration of 9 ns or less, and a pulse interval of 0.2 seconds.

* * * * *